United States Patent
Singh et al.

(10) Patent No.: US 7,263,168 B2
(45) Date of Patent: Aug. 28, 2007

(54) X-RAY IMAGING APPARATUS, COLLISION DETECTING DEVICE, AND DAMPER

(75) Inventors: Ram Kishan Singh, Bangalore (IN);
Bindu Santha Philip, Bangalore (IN);
Vipin J Pillai, Bangalore (IN); David Barker, Salt Lake City, UT (US);
Lonnie Weston, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 86 days.

(21) Appl. No.: 10/963,329

(22) Filed: Oct. 12, 2004

(65) Prior Publication Data
US 2005/0078800 A1   Apr. 14, 2005

(30) Foreign Application Priority Data
Oct. 14, 2003   (JP)   ............... 2003-353291

(51) Int. Cl.
*H05G 1/02* (2006.01)
*H01J 31/50* (2006.01)

(52) U.S. Cl. ............ 378/117; 378/20; 378/177; 378/189; 378/195; 378/197; 250/363.02

(58) Field of Classification Search ........ 378/20, 378/117, 177, 189, 195, 197; 250/363.02
See application file for complete search history.

(56) References Cited

U.S. PATENT DOCUMENTS

| | | | | |
|---|---|---|---|---|
| 4,811,725 A | * | 3/1989 | Grasser | ............... 601/4 |
| 4,987,583 A | * | 1/1991 | Travanty et al. | ............ 378/91 |
| 5,019,804 A | | 5/1991 | Fraden | |
| 5,056,365 A | * | 10/1991 | Gray et al. | ........... 73/432.1 |
| 5,097,495 A | | 3/1992 | Gray et al. | |
| 5,105,455 A | | 4/1992 | Kato et al. | |
| 5,486,700 A | | 1/1996 | Silberklang et al. | |
| 5,651,044 A | * | 7/1997 | Klotz et al. | ............ 378/117 |
| 5,805,658 A | | 9/1998 | Hum et al. | |
| 6,561,301 B1 | * | 5/2003 | Hattori et al. | ............ 180/274 |
| 6,594,615 B2 | | 7/2003 | Bernard et al. | |

FOREIGN PATENT DOCUMENTS

JP   HEISEI 4-061754   2/1992

OTHER PUBLICATIONS

An English Translation of a portion of JP Heisei 4-061754.

* cited by examiner

*Primary Examiner*—Edward J. Glick
*Assistant Examiner*—Thomas R. Artman
(74) *Attorney, Agent, or Firm*—Armstrong Teasdale LLP

(57) ABSTRACT

A collision detecting device includes a damper which is a hollow member with a fluid sealed into the interior thereof, and is formed, on its side abutted against an object to which it is to be mounted, in a concave shape conforming to the shape of a corner of the object, and is formed, on its side opposite to the concave shape, in a convex shape conforming to the shape of the corner of the object; and a detecting section for detecting an internal pressure of the damper.

20 Claims, 5 Drawing Sheets

X-RAY IMAGING APPARATUS, COLLISION DETECTING DEVICE, AND DAMPER

CROSS REFERENCE TO RELATED APPLICATIONS

This application claims the benefit of Japanese Application No. 2003-353291 filed Oct. 14, 2003.

BACKGROUND OF THE INVENTION

The present invention relates to an X-ray imaging apparatus, a collision detecting device, and a damper. Particularly, the present invention is concerned with an X-ray imaging apparatus provided with a device for detecting collision of an X-ray receiver with an obstacle, as well as such a collision detecting device and a damper for damping collision with an obstacle.

In an X-ray imaging apparatus wherein an X-ray irradiator and an X-ray receiver are attached respectively to both ends of a C-shaped arm so as to be opposed to each other, and an object is disposed between the X-ray irradiator and the X-ray receiver to perform fluoroscopic radiography, a sensor is disposed in the X-ray receiver to detect approaching or collision of the X-ray receiver with respect to the object (see, for example, Patent Literature 1).

[Patent Literature 1] Specification and drawings (Columns 3 to 8 and FIGS. 2 and 3) of U.S. Pat. No. 5,651,044

In the above X-ray imaging apparatus, the sensor is made up of plural electrodes and detection is performed while switching combinations of those plural electrodes from one to another by means of a multiplexer. Consequently, the construction of the detecting device is complicated.

SUMMARY OF THE INVENTION

Therefore, it is an object of the present invention to provide an X-ray imaging apparatus provided with a collision detecting device of a simple construction, as well as such a collision detecting device and a damper for the collision detecting device.

(1) For achieving the above-mentioned object, in one aspect of the present invention there is provided an X-ray imaging apparatus comprising an X-ray irradiator; an X-ray receiver; a support means for supporting the X-ray irradiator and the X-ray receiver in such a manner that the X-ray irradiator and the X-ray receiver are opposed to each other through a space, the support means permitting the X-ray receiver to approach an object to be radiographed located within the space; a damper which is a hollow member disposed at an object-side end portion of the X-ray receiver and with a fluid sealed into the interior thereof, the damper being formed, on its side abutted against the X-ray receiver, in a concave shape conforming to the shape of a corner of the X-ray receiver, and being formed, on its side opposite to the concave shape, in a convex shape conforming to the shape of the corner of the X-ray receiver; and a detecting means for detecting an internal pressure of the damper.

(2) For achieving the foregoing object, in another aspect of the present invention there is provided a collision detecting device comprising a damper which is a hollow member with a fluid sealed into the interior thereof, the damper being formed, on its side abutted against an object to which it is to be mounted, in a concave shape conforming to the shape of a corner of the object, and being formed, on its side opposite to the concave shape, in a convex shape conforming to the shape of the corner of the object; and a detecting means for detecting an internal pressure of the damper.

(3) For achieving the foregoing object, in a further aspect of the present invention there is provided a damper comprising a hollow member with a fluid sealed into the interior thereof, the damper being formed, on its side abutted against an object to which it is to be mounted, in a concave shape conforming to the shape of a corner of the object, and being formed, on its side opposite to the object, in a convex shape conforming to the shape of the corner of the object.

It is preferable that the hollow member be formed in the shape of a ring extending along an edge of the object to which it is to be mounted. This is because damping or collision detection can be done throughout the whole edge of the object. For morphological simplicity it is preferable that the ring be a circular ring. Further, it is preferable that the fluid be air, because the cost for the supply of the fluid is less expensive.

In the above aspect (1) there can be realized an X-ray imaging apparatus provided with a collision detecting device of a simple construction, by comprising: a damper which is a hollow member disposed at an object-side end portion of the X-ray receiver and with a fluid sealed into the interior thereof, the damper being formed, on its side abutted against the X-ray receiver, in a concave shape conforming to the shape of a corner of the X-ray receiver, and being formed, on its side opposite to the concave shape, in a convex shape conforming to the shape of the corner of the X-ray receiver; and a detecting means for detecting an internal pressure of the damper.

In the above aspect (2) there can be realized a collision detecting device of a simple construction by comprising: a damper which is a hollow member with a fluid sealed into the interior thereof, and is formed, on its side abutted against an object to which it is to be mounted, in a concave shape conforming to the shape of a corner of the object, and is formed, on its side opposite to the concave shape, in a convex shape conforming to the shape of the corner of the object; and a detecting means for detecting an internal pressure of the damper.

In the above aspect (3) there can be realized a damper suitable for the collision detecting device because the damper comprises a hollow member with a fluid sealed into the interior thereof, is formed, on its side abutted against an object to which it is to be mounted, in a concave shape conforming to the shape of a corner of the object, and is formed, on its side opposite to the object, in a convex shape conforming to the shape of the corner of the object.

Further objects and advantages of the present invention will be apparent from the following description of the preferred embodiments of the invention as illustrated in the accompanying drawings.

DETAILED DESCRIPTION OF THE INVENTION

Figure 1:
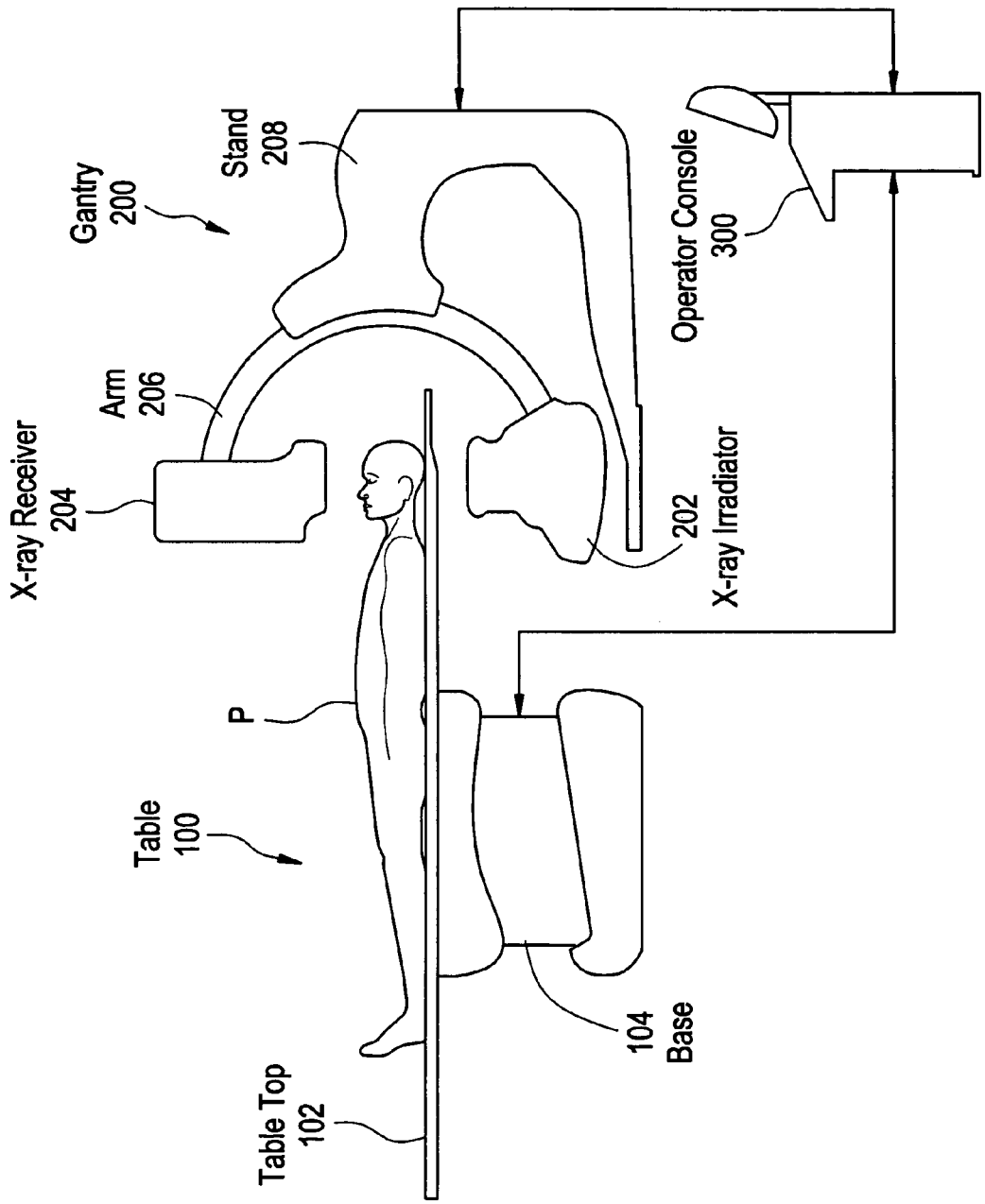
FIG. 1 illustrates a schematic construction of an X-ray imaging apparatus.

An embodiment of the present invention will be described in detail hereinunder. FIG. 1 illustrates a schematic construction of an X-ray imaging apparatus embodying the invention. The apparatus is one example of the mode for carrying out the X-ray imaging apparatus of the present invention. By the following construction of the apparatus there is shown one example of the mode for carrying out the invention with respect to the apparatus of the invention.

As shown in FIG. 1, the X-ray imaging apparatus has a table 100, a gantry 200, and an operator console 300.

The table 100 has a table top 102, on which an object P to be radiographed is placed face up. The table top 102 is supported by a base 104. In the interior of the base 104 there are disposed an advancing/retreating mechanism, a raising/lowering mechanism, and a tilting mechanism. These mechanisms respectively function to advance and retreat, raise and lower, and tilt the table top 102.

The gantry 200 supports mutually opposed X-ray irradiator 202 and X-ray receiver 204 through an arcuate, i.e., C-shaped, arm 206. The arm 206 is supported by a stand 208.

A drive mechanism for the arm 206 is disposed in the interior of the stand 208. With the drive mechanism, the arm 206 can perform arcuate motion (hereinafter referred to as "orbital motion"), rotational motion centered on a horizontal shaft, and vertical motion.

The X-ray irradiator 202 contains an X-ray tube to radiate X-ray toward the X-ray receiver 204. The X-ray receiver 204 contains an image intensifier and receives the X-ray emitted from the X-ray irradiator 202. For example, the X-ray receiver 204 has a generally cylindrical shape.

The X-ray irradiator 202 is an example of a mode for carrying out the invention with respect to the X-ray irradiator in the invention. The X-ray receiver 204 is an example of a mode for carrying out the invention with respect to the X-ray receiver in the invention. The arm 206 and the stand 208 are an example of a mode for carrying out the invention with respect to the support means in the invention.

The operator console 300 is a man machine interface for a user. The operator console 300 contains an information processor, e.g., a computer, and peripheral devices thereof and, in accordance with instructions given by a user, controls the table 100 and the gantry 200 and executes radiographing.

Figure 2:
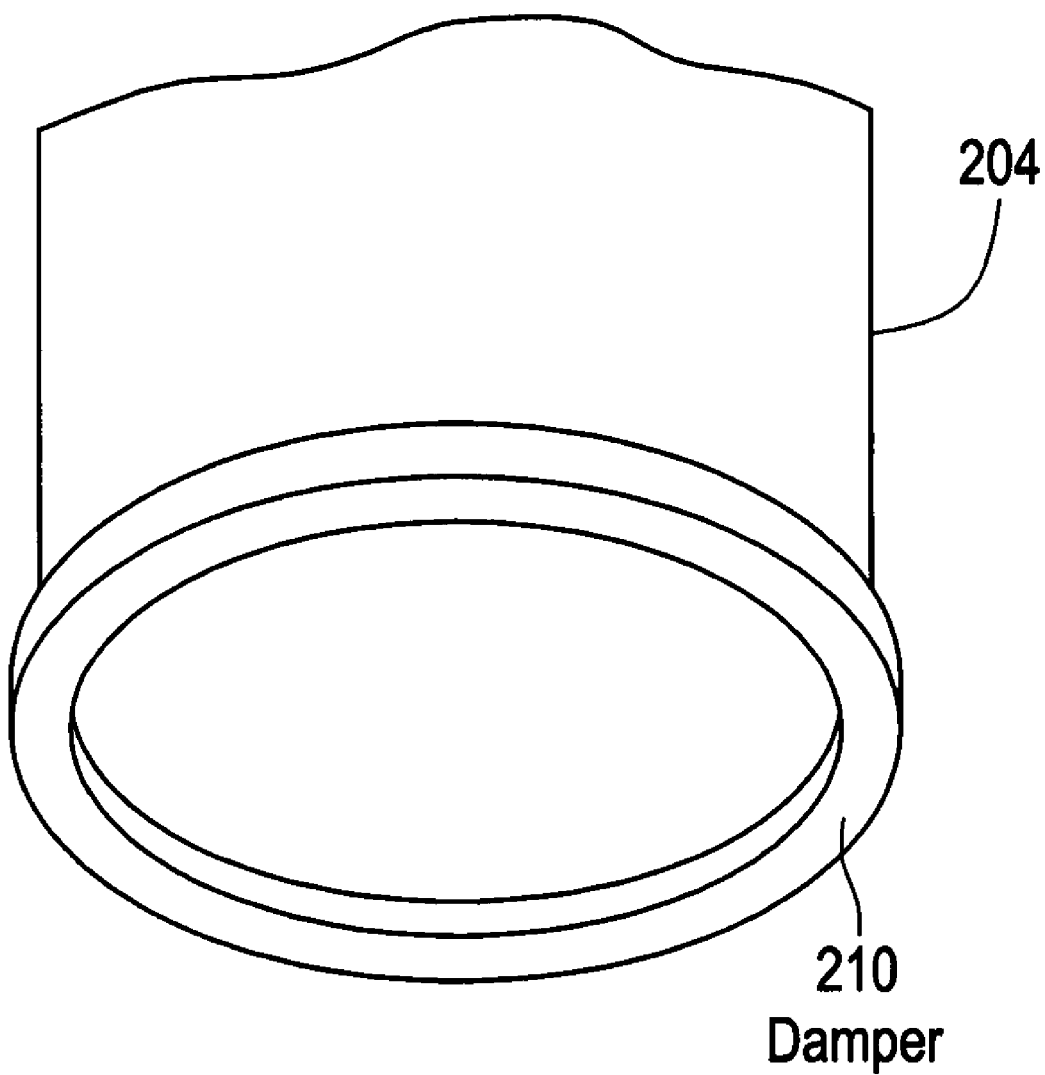
FIG. 2 illustrates a schematic construction of a damper used in the X-ray imaging apparatus.

This apparatus is provided with a collision detecting device. Reference will be made below to the collision detecting device. FIG. 2 illustrates a schematic construction of a damper which constitutes a part of the collision detecting device. As shown in the same figure, a damper 210 is provided at one end portion of the X-ray receiver 204. This portion is an end portion on the side where the X-ray receiver 204 confronts the object P, i.e., on the light receiving side.

The damper 210 is an example of a mode for carrying out the invention with respect to the damper therein. By the construction of this device there is shown an example of a mode for carrying out the invention with respect to the damper therein.

The damper 210 is disposed along an edge of an end portion of the X-ray receiver 204. The damper 210 has a circular ring profile conforming to the shape of an outer periphery of the end portion of the X-ray receiver 204, whereby the shape of the damper 210 is simplified. In the case where the shape of the outer periphery of the end portion of the X-ray receiver 204 is other than a circular shape, such as a square or rectangular shape, the damper 210 has a ring shape conforming to such a shape.

The damper 210 may be attached to not only the X-ray receiver 204 but also various movable members which may collide with an obstacle, to damp a collision shock. A description will be given below of the case where the damper 210 is attached to the X-ray receiver 204, but this is also true of the case where the damper is attached to other movable members.

Figure 3:
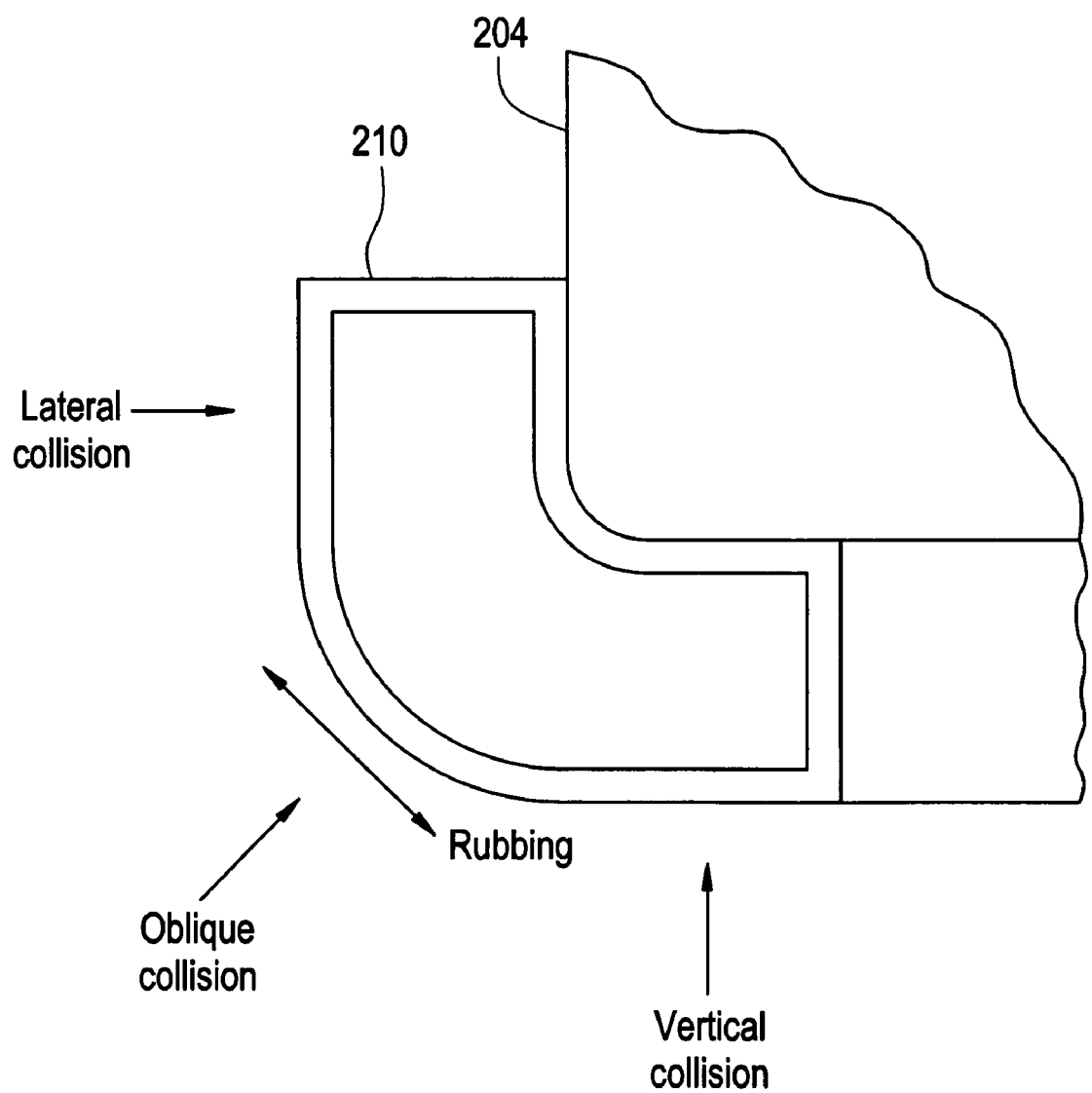
FIG. 3 illustrates a schematic construction of the damper in the X-ray imaging apparatus.

FIG. 3 is an enlarged sectional view showing a schematic construction of the portion where the damper 210 is disposed. As shown in the same figure, on the side (inside) where the damper 210 is abutted against the X-ray receiver 204, the damper is concave in conformity with the shape of a corner of the X-ray receiver 204, while on the side (outside) opposite thereto the damper 210 is convex in conformity with the shape of the corner of the X-ray receiver 204.

Thus, the damper 210 has an L-shaped cross section. Consequently, as indicated with arrows in FIG. 3, the damper 210 exhibits a damping action against collision in vertical, lateral and oblique directions and also against rubbing at the corner.

The damper 210 is formed of an elastic material such as rubber for example. The interior of the damper 210 is hollow, into which a fluid is sealed. For example, air is used as the fluid. The use of air is preferred because the supply of air is inexpensive. Of course, no limitation is made to air, but there may be used any other suitable gas or liquid.

Figure 4:
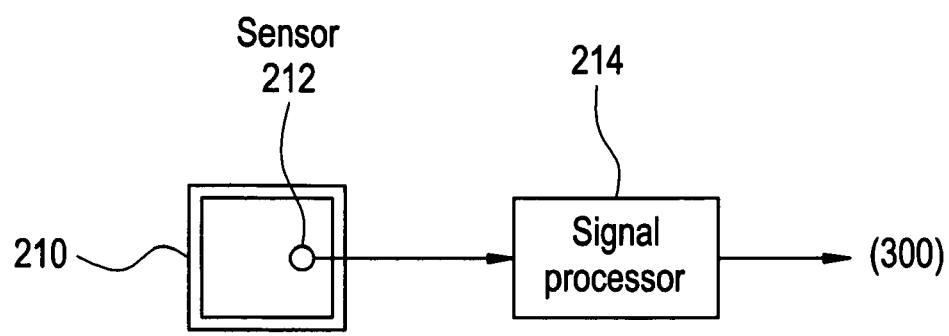
FIG. 4 is a block diagram of a collision detecting device.

FIG. 4 is a block diagram of a collision detecting device which uses the damper 210. This collision detecting device is an example of a mode for carrying out the invention with respect to the collision detecting device therein. By the construction of this device, there is shown an example of a mode for carrying out the invention with respect to the collision detecting device therein.

As shown in the same figure, the collision detecting device has a sensor 212 which is combined with the damper 210, and a signal processor 214. The sensor 212 is adapted to detect the pressure of the hollow portion of the damper 210. A detected signal provided from the sensor 212 is processed by the signal processor 214, whereby detection whether collision has occurred or not is performed.

More specifically, if some portion of the damper 210 collides with or rubs the object P, the damper 210 is compressed and the pressure of the hollow portion rises. In accordance with this pressure rise the signal processor 214 outputs a collision detection signal. The sensor 212 and the signal processor 214 show one example of the detecting means in the present invention. Since the collision detecting device thus detects whether collision has occurred or not on the basis of an internal pressure of the damper 210, the construction thereof is extremely simple.

The collision detection signal is transmitted to the operator console 300, which in turn stops the motion of the table 100 and the gantry 200 in accordance with the collision detection signal, to thereby prevent the object P from being injured. Further, the occurrence of collision or the like is displayed using a suitable means. At this time the damper 210 is in contact with the object P, but there is no fear of the object P being injured because the damper 210 has elasticity.

Figure 5:
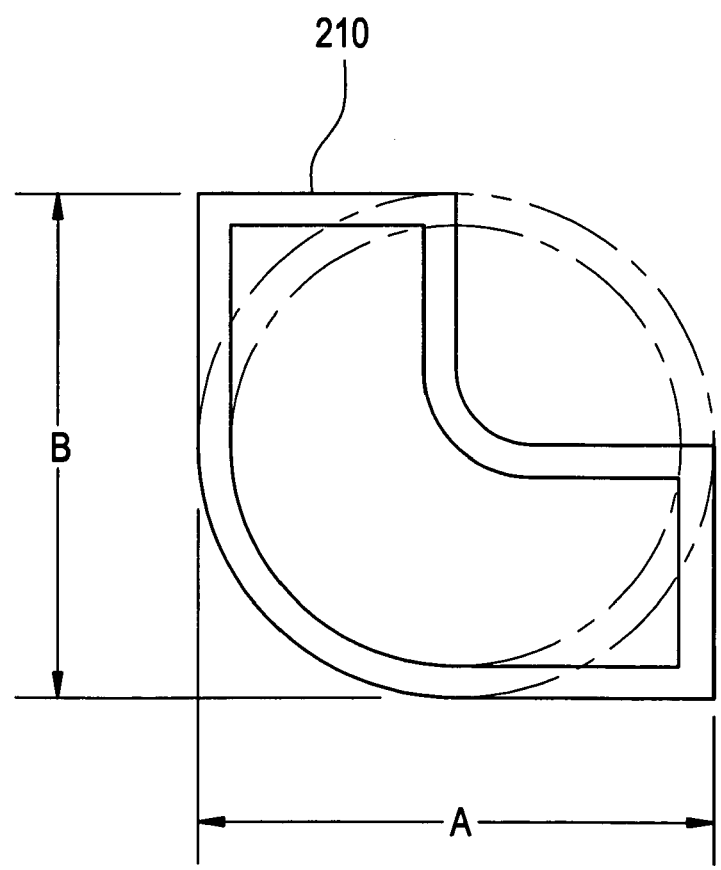
FIG. 5 illustrates a comparison of sectional shapes.

A description will now be given of advantages of the damper 210 which has an L-shaped section. As shown in FIG. 5, the damper 210 has a vertical collision detecting range A and a lateral collision detecting range B. The same detection ranges can also be realized even by using a damper having such a circular section (A=B) as indicated with dot-dash lines or an elliptic section (A≠B). However, the damper 210 having an L-shaped section is superior in softness at collision to the damper having a circular or elliptic section.

This is for the following reason. In the damper having a circular or elliptic section, the ratio of surface area to volume is low and a load dispersion area is small, so that the damper is deficient in softness. In contrast therewith, the damper 210 having an L-shaped section is higher in the surface area to volume ratio than the damper of a circular or elliptic section and is therefore softer. Moreover, since the surface area to volume ratio is higher, the detection sensitivity to collision and rubbing is also high.

Further, since the inside of the damper 210 of an L-shaped section is concave in conformity with a corner of the X-ray receiver 204, the amount of its projection from an outer wall of the X-ray receiver 204 is smaller than that of the damper of a circular or elliptic section.

Figure 6:
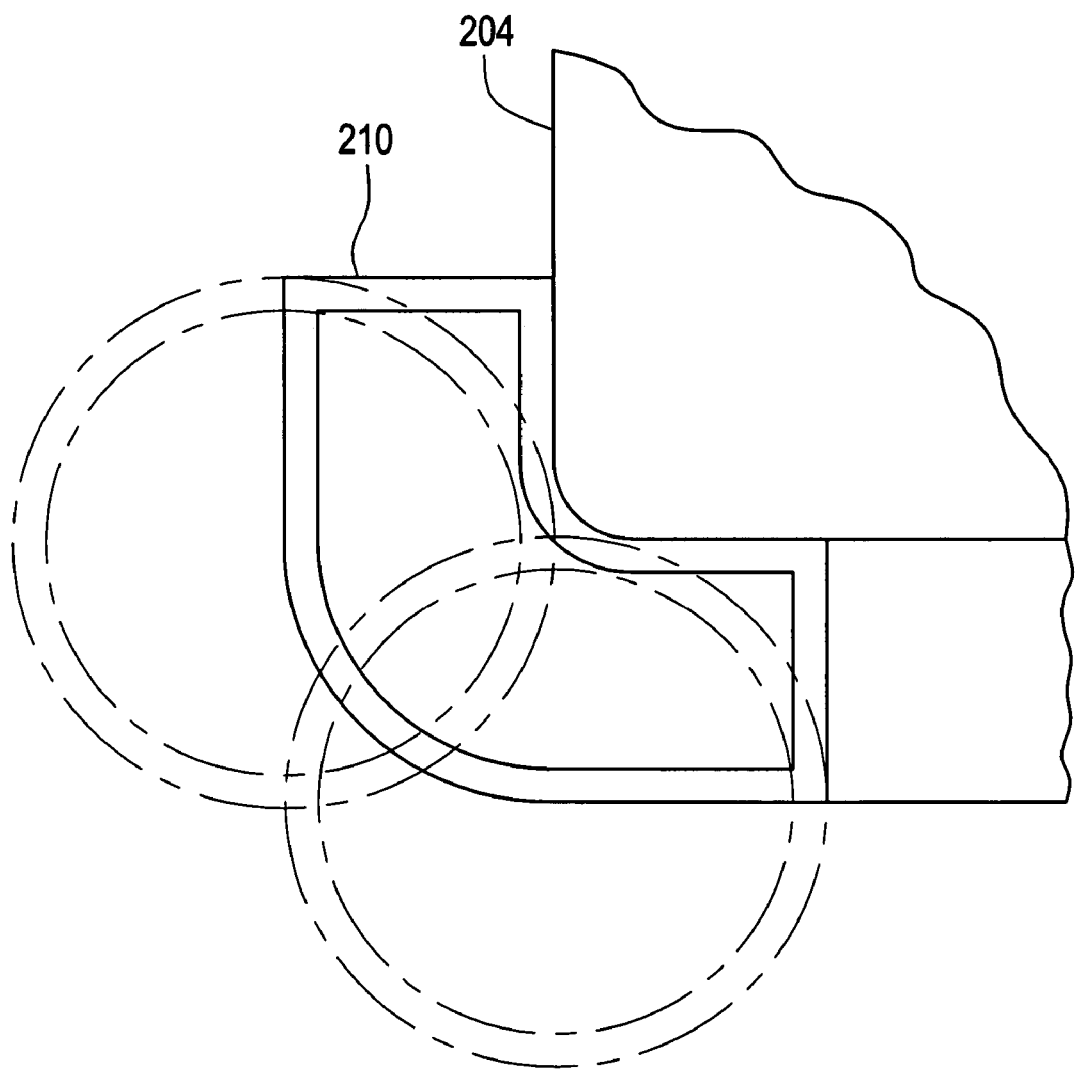
FIG. 6 also illustrates a comparison of sectional shapes.

More specifically, when the damper of a circular or elliptic section is attached to the X-ray receiver 204, as indicated with dot-dash lines in FIG. 6, the damper of a circular or elliptic section projects to a greater extent than the damper 210 in vertical or lateral direction from the outer wall of the X-ray receiver 204.

It is preferable that the amount of projection of the damper 210 be as small as possible because it restricts the closest distance of the X-ray receiver 204 to the object P. Also in this point the damper 210, which is smaller in the amount of projection from the outer wall of the X-ray receiver 204, is superior to the damper of a circular or elliptic section.

Many widely different embodiments of the invention may be constructed without departing from the spirit and the scope of the present invention. It should be understood that the present invention is not limited to the specific embodiments described in the specification, except as defined in the appended claims.

What is claimed is:

1. An X-ray imaging apparatus comprising:
   an X-ray irradiator;
   an X-ray receiver;
   a support section for supporting the X-ray irradiator and the X-ray receiver in such a manner that the X-ray irradiator and the X-ray receiver are opposed to each other through a space, the support section permitting the X-ray receiver to approach an object to be radiographed located within the space;
   a damper comprising a unitarily-formed hollow member having an opening defined by a closed cross-sectional configuration of the damper, the damper disposed at an object-side end portion of the X-ray receiver and with a fluid sealed into an interior of the opening, wherein the entire damper is made of an elastic material and has a first side abutted against the X-ray receiver, wherein the first side has a concave shape conforming to a shape of a corner of the X-ray receiver, wherein the damper has a second side opposite to the first side, wherein the second side has a convex shape conforming to the shape of the corner of the X-ray receiver; and
   a detecting section for detecting an internal pressure of the damper.

2. An X-ray imaging apparatus according to claim 1, wherein the hollow member has a shape of a ring extending along an edge of the X-ray receiver.

3. An X-ray imaging apparatus according to claim 2, wherein the ring is a circular ring.

4. An X-ray imaging apparatus according to claim 1, wherein the fluid is air.

5. An X-ray imaging apparatus according to claim 1, wherein the elastic material is rubber.

6. An X-ray imaging apparatus according to claim 1, wherein the ring is a rectangular ring.

7. An X-ray imaging apparatus according to claim 1, wherein the damper further comprises a lateral surface and a vertical surface.

8. An X-ray imaging apparatus according to claim 1, wherein the detection section further comprises a pressure sensor.

9. An X-ray imaging apparatus according to claim 1, wherein the detection section is configured to generate a collision detection signal.

10. An X-ray imaging apparatus according to claim 1, further comprising a signal processor configured to receive a collision detection signal transmitted by the detection section.

11. An X-ray imaging apparatus according to claim 10, wherein the signal processor is further configured to determine whether a collision has occurred between the damper and an object.

12. An X-ray imaging apparatus according to claim 1, further comprising an operation console configured to receive a collision detection signal from a signal processor and to control a motion of said X-ray imaging apparatus based on the received collision detection signal.

13. A collision detecting device comprising:
   a damper comprising a unitarily-formed hollow member having an opening defined by a closed cross-sectional configuration of the damper with a fluid sealed into an interior of the opening, wherein the entire damper is made of an elastic material and has a first side abutted against an object to which it is to be mounted, wherein the first side has a concave shape conforming to a shape of a corner of the object and is L-shaped, wherein the damper has a second side opposite to the first side, and wherein the second side has a convex shape conforming to the shape of the coma of the object; and a detecting section for detecting an internal pressure of the damper.

14. A collision detecting device according to claim 13, wherein the hollow member has a shape of a ring extending along an edge of the object.

15. A collision detecting device according to claim 14, wherein the ring is a circular ring.

16. A collision detecting device according to claim 13, wherein the fluid is air.

17. A damper comprising a unitarily-formed hollow member having an opening defined by a closed cross-sectional configuration of the damper with a fluid sealed into an interior of the opening, wherein the entire damper is made of an elastic material and has a first side abutted against an object to which it is to be mounted, wherein the first side has a concave shape conforming to a shape of a corner of the object and is L-shaped, wherein the damper has a second side opposite to the object, and wherein the second side has a convex shape conforming to the shape of the corner of the object.

18. A damper according to claim 17, wherein the hollow member has a shape of a ring extending along an edge of the object to which it is to be mounted.

19. A damper according to claim 18, wherein the ring is a circular ring.

20. A damper according to claim 17, wherein the fluid is air.

* * * * *

UNITED STATES PATENT AND TRADEMARK OFFICE
CERTIFICATE OF CORRECTION

PATENT NO. : 7,263,168 B2 Page 1 of 1
APPLICATION NO. : 10/963329
DATED : August 28, 2007
INVENTOR(S) : Singh et al.

It is certified that error appears in the above-identified patent and that said Letters Patent is hereby corrected as shown below:

Column 6, line 38, delete "coma" and insert therefor -- corner --.

Signed and Sealed this

Twenty-ninth Day of April, 2008

JON W. DUDAS
*Director of the United States Patent and Trademark Office*